(12) United States Patent
Chen

(10) Patent No.: US 7,604,647 B2
(45) Date of Patent: Oct. 20, 2009

(54) OPHTHALMIC CANNULA INSERTION TOOL AND METHOD

(75) Inventor: David E. Chen, Fremont, CA (US)

(73) Assignee: Medical Instrument Development Laboratories, Inc., San Leandro, CA (US)

( * ) Notice: Subject to any disclaimer, the term of this patent is extended or adjusted under 35 U.S.C. 154(b) by 211 days.

(21) Appl. No.: 10/971,421

(22) Filed: Oct. 22, 2004

(65) Prior Publication Data

US 2006/0089607 A1   Apr. 27, 2006

(51) Int. Cl.
*A61F 9/007* (2006.01)

(52) U.S. Cl. .................................. 606/166; 606/181

(58) Field of Classification Search ............... 606/166, 606/167, 181, 185, 172, 182, 107, 130, 133; 604/136, 156, 157, 6.05, 46, 181, 187, 264, 604/272, 383, 403, 411, 414; 600/583, 573; 30/162, 320
See application file for complete search history.

(56) References Cited

U.S. PATENT DOCUMENTS

| | | | |
|---|---|---|---|
| 1,434,388 A * | 11/1922 | Hughes | ..................... 30/320 |
| 3,190,661 A | 6/1965 | Wahl et al. | |
| 3,313,299 A | 4/1967 | Spademan | |
| 3,510,177 A | 5/1970 | Shimula | |
| 3,568,436 A | 3/1971 | Heffner et al. | |
| 3,776,238 A | 12/1973 | Payman et al. | |
| 3,815,604 A | 6/1974 | O'Malley et al. | |
| 3,829,104 A | 8/1974 | Green | |
| 3,853,127 A | 12/1974 | Spademan | |
| 3,884,238 A | 5/1975 | O'Malley et al. | |
| 4,011,869 A | 3/1977 | Seller, Jr. | |
| 4,146,237 A | 3/1979 | Bergman | |
| 4,177,814 A | 12/1979 | Knepshield et al. | |
| 4,222,575 A | 9/1980 | Sekiguchi et al. | |

(Continued)

FOREIGN PATENT DOCUMENTS

WO   WO 01/68016   9/2001

(Continued)

OTHER PUBLICATIONS

N. G. Pallucci, Description d'un nouvel instrument propre a abraiser la cataracte avec tout le succes possible. Paris: Son of d'Houry, 1750.

(Continued)

*Primary Examiner*—Anhtuan T Nguyen
*Assistant Examiner*—Ryan J Severson
(74) *Attorney, Agent, or Firm*—Michael Best & Friedrich LLP

(57) ABSTRACT

A cannula insertion tool having a needle movable between a retracted position and an extended position. In some embodiments, the needle can be retracted within the periphery of a handle of the insertion tool when not in use to protect the needle. When the needle is needed for surgical use, the needle can be extended at least partially beyond the outer periphery of the handle. The needle can be coupled to a slide movable relative to the handle between the retracted position and the extended position. The slide can be secured in each position to prevent unintentional movement of the slide. A cannula can be positioned on the needle when the needle is in the retracted position, and can be retained upon the needle by a member extending toward the cannula.

20 Claims, 3 Drawing Sheets

U.S. PATENT DOCUMENTS

| | | | |
|---|---|---|---|
| 4,413,829 | A | 11/1983 | Pietsch |
| 4,530,359 | A | 7/1985 | Helfgott et al. |
| 4,590,935 | A | 5/1986 | Ranalli |
| 4,653,513 | A * | 3/1987 | Dombrowski ............... 600/578 |
| 4,655,743 | A | 4/1987 | Hyde |
| 4,655,752 | A | 4/1987 | Honkanen et al. |
| 4,693,343 | A | 9/1987 | Boyd |
| 4,696,298 | A | 9/1987 | Higgins et al. |
| 4,756,536 | A | 7/1988 | Belcher |
| 4,759,359 | A * | 7/1988 | Willis et al. ................. 606/107 |
| 4,819,635 | A | 4/1989 | Shapiro |
| 4,895,147 | A * | 1/1990 | Bodicky et al. ............. 606/182 |
| 4,958,625 | A * | 9/1990 | Bates et al. ................. 600/567 |
| 5,009,435 | A | 4/1991 | Villanyi et al. |
| 5,019,035 | A | 5/1991 | Missirlian et al. |
| 5,041,095 | A | 8/1991 | Littrell |
| 5,176,628 | A | 1/1993 | Charles et al. |
| 5,284,472 | A | 2/1994 | Sussman et al. |
| 5,547,473 | A | 8/1996 | Peyman |
| 5,752,938 | A | 5/1998 | Flatland et al. |
| 5,803,919 | A | 9/1998 | Hart et al. |
| 5,843,111 | A | 12/1998 | Vijfvinkel |
| 5,979,494 | A | 11/1999 | Perkins et al. |
| 6,006,433 | A * | 12/1999 | Baltazar ...................... 30/162 |
| 6,139,560 | A | 10/2000 | Kremer |
| 6,439,541 | B1 | 8/2002 | Nösel et al. |
| 6,561,519 | B1 | 5/2003 | Frese et al. |
| 6,575,990 | B1 | 6/2003 | Wang et al. |
| 6,602,268 | B2 * | 8/2003 | Kuhr et al. .................. 606/181 |
| 2004/0092982 | A1 | 5/2004 | Sheffer |

OTHER PUBLICATIONS

R. Machemer, H. Buettner, E. W. Norton, J. M. Parel, Vitrectomy: A Pars Plana Approach. Trans Am Acad Ophthalmol Otolaryngol. 75(4):813-20, 1971.

N. G. Douvas, Microsurgical Pars Plana Lensectomy. Transactions American Academy of Ophthalmol Otolaryngol., vol. No. 81, 3 pages (3 Pt 1):371-381, 1976.

R. Machemer, D. Hickingbotham, The Three-Port Microcannular System for Closed Vitrectomy. Am J Ophthalmol. 100(4):590-2, 1985.

K. M. Zinn, A. Grinblat, H. M. Katzin, M. Epstein, C. Kot, A New Endoillumination Infusion Cannula for Pars Plana Vitrectomy. Ophthalmic Surg. 11(12):850-5, 1980.

M. W. Gaynon, C. L. Schepens, T. Hirose, Four-Port Bimanual Vitrectomy. Arch Ophthalmol. 104(7):1088-9, 1986.

Motorola Linear/Interface Devices, published prior to Oct. 21, 2004.

* cited by examiner

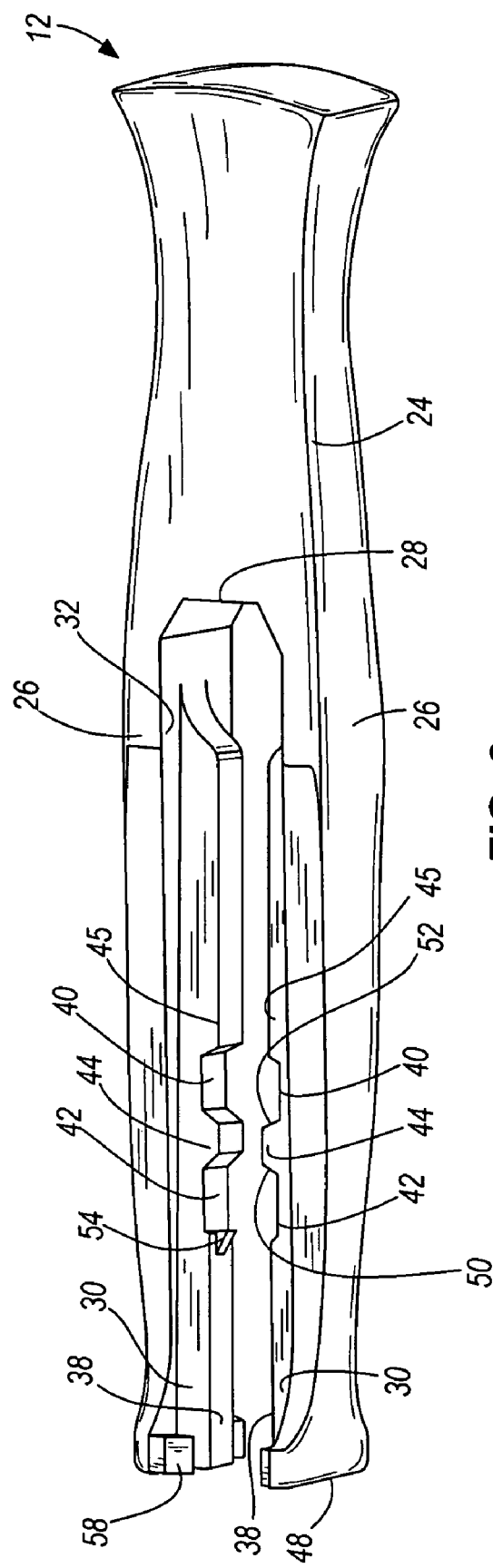
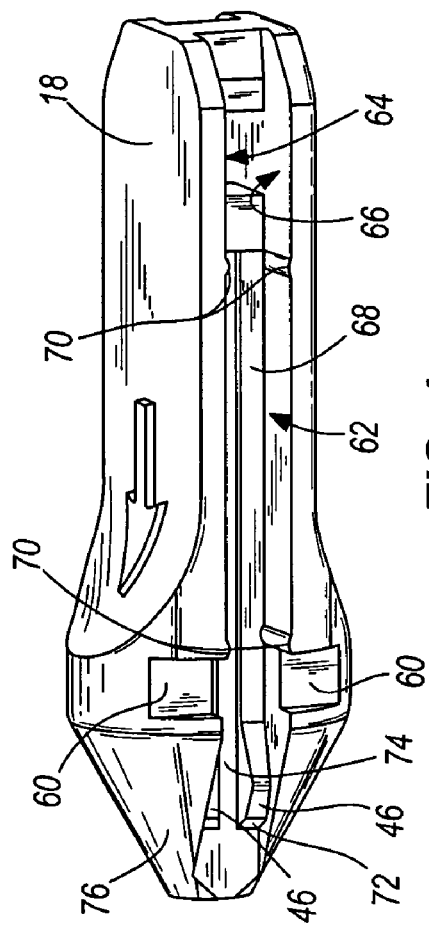

OPHTHALMIC CANNULA INSERTION TOOL AND METHOD

FIELD OF THE INVENTION

Embodiments of the invention relate to aspects of improved trocar-cannula devices for use in surgery of the posterior segment of the eye.

BACKGROUND OF THE INVENTION

A trocar-cannula is a surgical instrument. It can be used to drain fluid from a body cavity, introduce fluids into the body cavity, and insert a tool into the body cavity to perform surgical functions. The trocar-cannula is often comprised of two principal parts: (1) a hollow tube or cannula and (2) a puncturing member referred to as an obturator or trocar. The cannula is inserted through the wall of the body cavity with the assistance of the trocar passed through the cannula.

A trocar-cannula may be used in cardiovascular surgery, laparoscopic surgery, arthroscopic surgery, and intraocular surgery. In intraocular surgery, for example, a trocar-cannula is often used to obtain access to the posterior-segment of the eye (area behind the lens). Typically, a cannula is positioned on a needle of a trocar for insertion into the eye. The needle is used to penetrate the eye and insert the cannula. Upon insertion of the cannula, the trocar can be removed from the eye while the cannula remains inserted in the eye.

SUMMARY OF THE INVENTION

Conventional ophthalmic trocars generally have a handle and a needle fixed to the handle. The needle of some conventional trocars can be protected by a cap that can be placed over the needle. However, since the cap can be separated from the trocar, the cap can be misplaced or otherwise prematurely removed from a position shielding the needle, thereby exposing the needle at undesirable times.

Some embodiments of the present invention provide a trocar having a needle that is protectable without the need for additional parts that can be separated from the trocar. In some embodiments, an ophthalmic trocar having a retractable needle is provided, wherein the needle can be retracted to a protected position within the periphery of a handle when not in use. When the needle is needed for surgical use, the needle can be extended at least partially beyond the outer periphery of the handle.

In some embodiments, the needle is coupled to a slide that is movable relative the handle between a retracted position and an extended position. In some cases, the slide can be secured in either or both positions. In the retracted position for example, the slide can be selectively secured to prevent unintentional movement of the slide to the extended position. In the extended position for example, the slide can be secured to prevent the slide from moving relative the handle during use of the trocar.

In some embodiments, the trocar has a cannula positioned on the needle when the needle is in the retracted position, and has a member positioned to prevent the cannula from inadvertently disengaging the needle in the retracted position.

These and other aspects of the embodiments of the invention, together with the organization and operation thereof, will become apparent from the following detailed description when taken in conjunction with the accompanying drawings.

BRIEF DESCRIPTION OF THE DRAWINGS

FIG. 3 is a perspective view of the handle of the trocar shown in FIG. 1.

FIG. 4 is a perspective view of the slide of the trocar shown in FIG. 1.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. Phraseology and terminology used herein with reference to device or element orientation (such as, for example, terms like "front", "back", "up", "down", "top", "bottom", and the like) are only used to simplify description of the present invention, and do not alone indicate or imply that the device or element referred to must have a particular orientation. Also, the use of "including," "comprising," or "having" and variations thereof is meant to encompass the items listed thereafter and equivalents thereof as well as additional items. The terms "mounted," "connected," and "coupled" are used broadly and encompass both direct and indirect mounting, connecting and coupling. Further, "connected" and "coupled" are not restricted to physical or mechanical connections or couplings.

DETAILED DESCRIPTION

Figure 1:
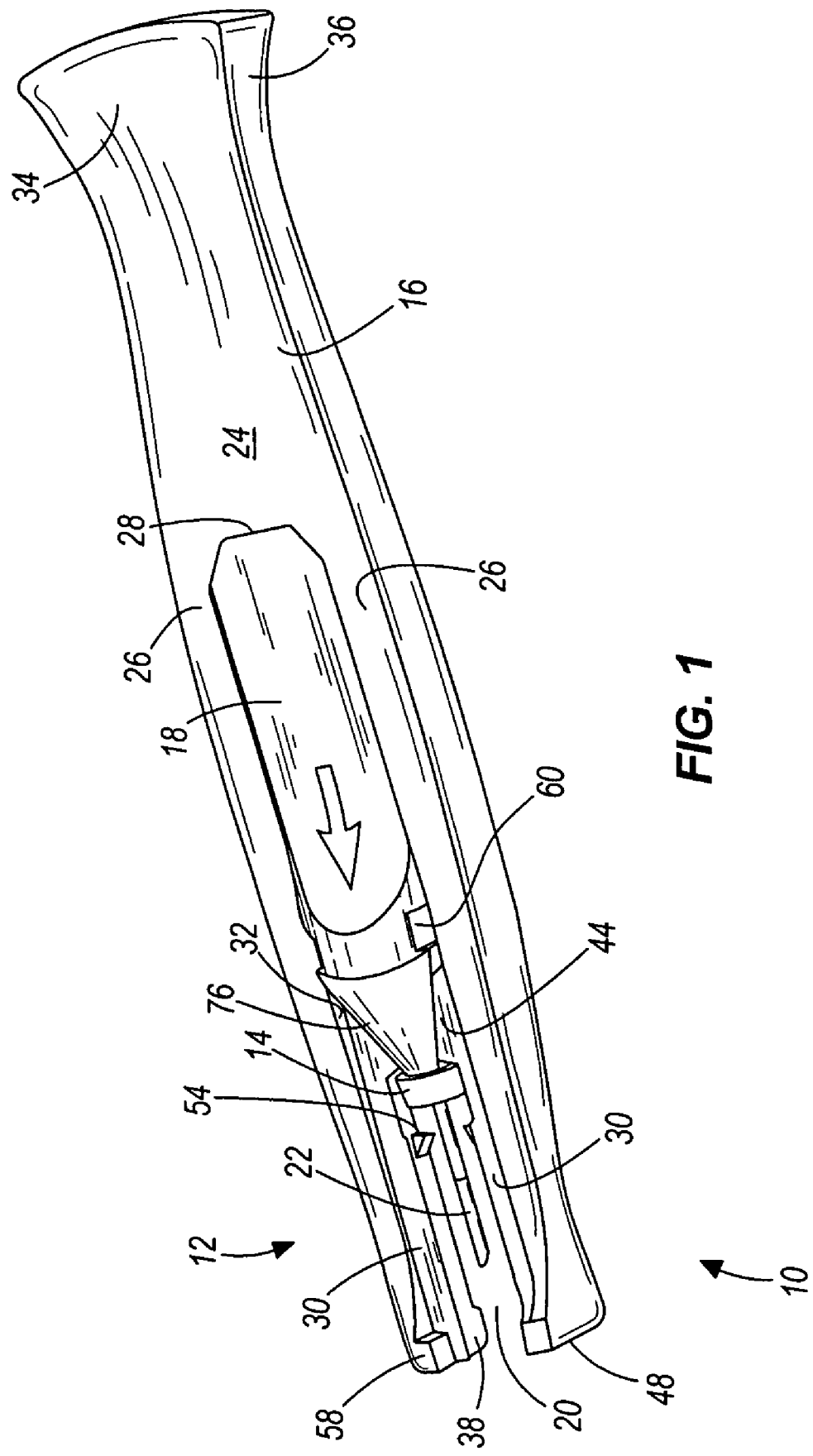
FIG. 1 is a perspective view of a trocar-cannula according to an embodiment of the present invention, wherein the needle of the trocar is shown in a retracted position with a cannula positioned on the needle.
Figure 2:
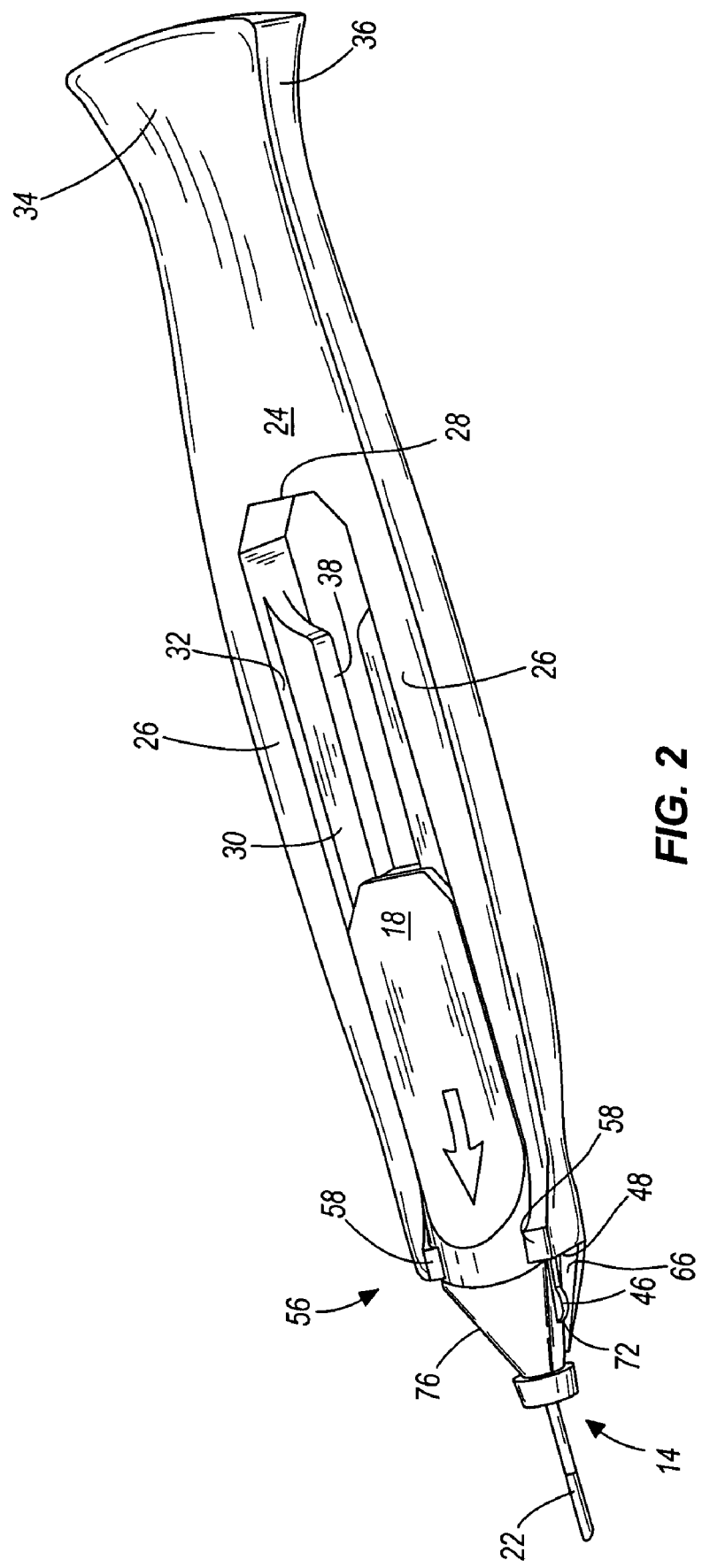
FIG. 2 is a perspective view of the trocar-cannula shown in FIG. 1, wherein the needle of the trocar is shown in an extended position.

With reference to FIG. 1, there is shown an ophthalmic trocar-cannula assembly 10 having a trocar 12 and a cannula 14. The trocar 12 includes a handle 16, a slide 18 moveable within an elongated aperture 20 of the handle 16, and a needle 22 coupled to the slide 18. The cannula 14 is adapted to be received on the needle 22 as shown in FIGS. 1 and 2 for insertion with the needle 22 into an eye.

The handle 16 in the illustrated embodiment includes a main body portion 24 and two arms 26 extending from an end 28 of the main body portion 24. The arms 26 can be integral with the main body portion 24 or can be separate elements attached to the main body portion in any suitable manner. Also, the arms 26 can be cantilevered from the main body portion 24 and extend from the end 28 of the main body portion in a longitudinal direction (e.g., wherein the ophthalmic trocar-cannula assembly 10 is elongated to define a longitudinal direction of the assembly 10). In the illustrated embodiment, the arms 26 at least partially define the elongated aperture 20 extending in the longitudinal direction.

With continued reference to FIGS. 1-4, the arms 26 each have a rib 30 that extends along the arm 26 in the longitudinal direction. The ribs 30 extend substantially the entire length of the arms 26, and extend from an inner surface 32 of the arms 26 into the elongated aperture 20. In other embodiments, the ribs 30 extend along less than the entire length of the arms 26, depending at least in part upon the desired range of motion of the slide 18 and upon the location of projections and recesses of the slide 18 and arms 26 (described in greater detail below). The ribs 30 can also be recessed relative to a top surface 34 and a bottom surface 36 of the handle 16 as shown in FIGS. 1-4.

As illustrated in FIG. 3, the inner longitudinally extending edge 38 of each rib 30 is interrupted by one or more recesses or projections. These projections and recesses help to retain the slide 18 and/or cannula 14 in desired positions with respect to the handle 16. For example, a pair of recesses 40, 42 can extend into each rib 30 on either side of a projection 44 that extends from the rib 30. Each rib 30 can also extend longitudinally away from a location 45 adjacent the recesses 40, 42. One of the recesses 40 in each rib 30 illustrated in FIG. 1-4 is defined by the projection 44 and another part of the rib 30, and engages a portion of the slide 18 when the slide 18 is in the retracted position (FIG. 1). Recess 40 receives one or more projections 46 on the slide 18 when the slide 18 is in the retracted position to prevent unintended movement of the slide 18 from the retracted position.

The recesses 40, 42 and the projection 44 are positioned along a portion of the rib 30 corresponding to the retracted position of the slide 18. In the illustrated embodiment, the recesses 40, 42 are located at a mid-portion of each arm 26. However, in other embodiments, the recesses 40, 42 can be located in other positions along the arms 26 (e.g., such as where the arms 26 engage the slide 18 at different longitudinal positions of the slide 18).

With the exception of the recesses 40, 42 described above, each rib 30 can have a substantially uniform cross-sectional shape along any part or all of the rib 30. With reference again to FIG. 3, recess 42 cuts transversely into the rib 30 and extends along the rib 30 in the longitudinal direction for a relatively short distance. A ramped surface 50 extends from the recess 42 to provide a transition between the recess 42 and an adjacent portion of the rib 30 having projection 44. The projection 44 only extends a relatively short distance in the longitudinal direction before being interrupted by the other recess 40. The projection 44 transitions into the recess 40 along a ramped surface 52. This recess 40 is approximately as deep as the recess 42 on the opposite side of the projection 44, although the recesses 40, 42 can have different depths in other embodiments. This remainder of the rib 30 (extending from location 45) can extend into the elongated aperture 20 substantially the same distance as the projection 44, or can extend to a greater or lesser distance in other embodiments.

As mentioned above, recess 40 is dimensioned and positioned to receive the projection 46 of the slide 18. When the projection 46 of the slide 18 is received within the recess 40, engagement between the projection 46 and the recess 40 prevents movement of the slide 18 from the retracted position. The ramped transition 52 between the recess 40 and the adjacent projection 44 helps to disengage the slide 18 from the retracted position upon application of a sufficient force to elastically deform the arms 26 of the handle 16.

As shown in FIGS. 1 and 3, an additional projection 54 can extend from one or more of the arms 26 to block the cannula 14 from inadvertent removal or from falling off the needle 22 when the needle 22 is in the retracted position. The projection (s) 54 can be located on the ribs 30 of the handle 16, or can extend from any other portion of the handle 16 to a location in which the cannula 14 is blocked from moving off the needle 22 in the retracted position. In the illustrated embodiment, for example, each projection 54 is positioned further toward the distal end 48 of each arm 26 than the recess 42, and extends from each rib 30 into the elongated aperture 20 toward the needle 22. In some embodiments, each projection 54 extends only partially into the elongated aperture 20. In other words, the projection 54 does not extend far enough to interfere or substantially interfere with movement of the needle 22. Rather, the projection 54 only extends to a position where it can block the cannula 14 from inadvertent movement off of the needle 22. Accordingly, the projection 54 prevents the cannula 14 from disengaging the needle 22 while the needle 22 is in the retracted position, and yet allows the cannula 14 to be moved past the projection 54 as the slide 18 is moved from the retracted position to the extended position.

A locking mechanism 56 can be positioned at the end 48 of each arm 26. The locking mechanism 56 can engage the slide 18 in the extended position and prevent the slide 18 from inadvertently returning to the retracted position. The locking mechanism 56 in the illustrated embodiment includes a projection 58 that extends from each arm 26 into the elongated aperture 20. These projections 58 are positioned and dimensioned to engage a portion of the slide 18 when the slide 18 is moved to the extended position. Specifically, the projections 58 each engage a respective recess 60 of the slide 18 to lock the slide 18 in the extended position. Accordingly, such engagement prevents movement of the slide 18 away from the extended position. Dependent at least in part upon the shape of the projections 58 and recesses 60, this engagement can prevent movement of the slide 18 back toward the retracted position and/or movement of the slide 18 further away from the retracted position (e.g., out of the elongated aperture 20). For example, none of the projections 58 and recesses 60 illustrated in the embodiment of FIGS. 1-4 have ramped surfaces. Therefore, the slide 18 illustrated in FIGS. 1-4 resists movement in either direction from the extended position once the projections 58 are engaged within the recesses 60.

As described above, the slide 18 is movable along the arms 26 between a retracted position and an extended position. The slide 18 is movable between these positions by sliding along the ribs 30 of the handle 16. As shown in FIG. 4, the slide 18 can have a main channel 62 that extends along each side of the slide 18 to receive the ribs 30 of the handle 16. The main channel 62 can be partially defined by upper and lower inner surfaces 64, 66 of the slide 18, as well as an interrupted longitudinally extending wall 68. The rib 30 is generally received within this area of the slide 18.

In some embodiments, one or more projections 70 extend from the upper and/or lower inner surfaces 64, 66 of the channel 62. In the illustrated embodiment, for example, a pair of projections 70 extend from each inner surface 64, 66 of the channel 62. These projections 70 can be spaced apart from each other in the longitudinal direction, and can be positioned and dimensioned to engage the ribs 30 and slide along the ribs 30. These projections reduce the amount of surface contact between the upper and lower inner surfaces 64, 66 of the channel 62 and the ribs 30, which can therefore reduce the sliding friction between the slide 18 and the ribs 30.

As discussed above, projections 46 also extend from the longitudinally extending surface 68 of the main channel 62. These projections 46 can be positioned near one end of the main channel 62 and extend in a transverse direction from the longitudinal surface 68 of the main channel 62. The projections 46 are dimensioned and positioned to engage the recesses 40 of the ribs 30 in the retracted position of the slide 18 as described above. Accordingly, the slide 18 can be held in the retracted position due to the engagement of the projections 46 with the recesses 40. The projections 46 can also have ramped surfaces 72. Engagement of the ramped surfaces 72 on the projections 46 and the ramped surfaces 52 on the recesses 40 allow the slide 18 to be forced from the retracted position to the extended position. In other embodiments, fewer ramped surfaces (e.g., ramped surfaces 72 only on the projections 46 or ramped surfaces 52 only on the recesses 40) can be used while still enabling movement of the slide 18 from the retracted position.

In some embodiments, an additional channel 74 extends along the slide 18 in the longitudinal direction. This channel 74 can be recessed into the main channel 62, and can be dimensioned and positioned to receive the projection 54 as the slide 18 is moved from the retracted position to the extended position.

As previously discussed, several recesses 60 can be positioned in the slide 18 for engagement with projections 58 of the handle 16 (adjacent the main channel 62 in the illustrated embodiment). The recesses 60 can be located on the outside surface of the slide 18 and are dimensioned and positioned to receive the projections 58 of the locking mechanism 56 when the slide 18 is in the extended position. In some embodiments, the slide 18 has one or more tapered surfaces 76 extending toward each recess 60. These tapered surfaces 76 can initiate engagement between the recesses 60 and the projections 58 of the locking mechanism 56. The tapered surfaces 76 can provide a transition that causes the arms 26 of the handle 16 to elastically expand until the recesses 60 receive the projections 58 of the locking mechanism 56. In this regard, the projections 58 elastically move into engagement with the recesses 60 to form an interlocking engagement between the slide 18 and the handle 16.

The needle 22 in the illustrated embodiment has a cylindrical shaft and a pointed tip, and extends from the end of the slide 18. The needle 22 can be coupled to the slide 18 in a number of different manners. For example, the needle 22 can be insert molded, press fit, or threaded upon or in the slide 18, can be attached to the slide by adhesive or cohesive bonding material, and the like. The needle 22 can move with the slide 18 between the retracted position and the extended position. When the slide 18 is in the retracted position, the needle 22 is stored within the periphery of the handle 16, thereby protecting the needle 22. When the slide 18 is moved to the extended position, the needle 22 extends beyond the periphery of the handle 16.

In some embodiments of the present invention, the trocar-cannula assembly 10 is assembled as follows. The needle 22 is coupled the slide 18, and the slide 18 is coupled the handle 16. The cannula 14 is also positioned on the shaft of the needle 22. The slide 18 is placed in the retracted position, where the engagement between the recesses 40 of the ribs 30 and the projections 46 of the slide 18 prevent inadvertent movement of the slide 18 from the retracted position. The slide 18 remains in the retracted position until the assembly 10 is ready to be used. Accordingly, the needle 22 is protected against damage. Furthermore, the cannula 14 is blocked from removal by the projection(s) 54 when the needle 22 is in the retracted position. Thus, the cannula 14 cannot be inadvertently disengaged from the trocar 12 while the needle 22 is in the retracted position.

During use of the trocar-cannula assembly 10 illustrated in FIGS. 1-4, the slide 18 is moved from the retracted position to the extended position by applying force to the slide 18 relative to the handle 16. Once sufficient force is applied to the slide 18, the ramped surfaces 52, 72 of the projections 46 on the slide and the recesses 40 in the ribs 30 begin to move relative to each other. This causes the arms 26 of the handle 16 to elastically expand, thereby allowing the projections 46 to disengage the recesses 40. Once the projections 46 disengage the recesses 40, the slide 18 can be moved toward the extended position. As the projections 46 of the slide 18 move past the projections 44 on each rib 30, the projections 46 of the slide 18 move along another ramped surface 50. This allows the arms 26 to elastically return to a non-biased position. Once the projections 46 on the slide 18 pass these projections 44 on the ribs 30, the slide 18 can move to the extended position relatively easily. As the slide 18 moves to the extended position, the needle 22 begins to extend from the periphery of the handle 16.

To use the trocar 12 to insert the cannula 14, the needle 22 and slide 18 are locked with respect to one another in the extended position. The slide 18 is locked in the extended position as the slide 18 is moved to the extended position. During this movement, the tapered end 76 of the slide 18 adjacent the needle 22 engages the projections 56 at the end 48 of each arm 26. The engagement of the tapered surfaces 76 with the projections 58 causes the arms 26 to move away from one another until the recesses 60 in the slide 18 align with the interlocking projection 58 of each arm 26. Upon alignment of these features, the arms 26 urge the projections 58 into the recesses 60. This interlocking relationship prevents relative movement between the slide 18 and the handle 16.

During insertion of the cannula 14 into an eye, the pointed tip of the needle 22 punctures the surface of the eye. The handle 16 of the trocar 12 is then pressed forward to further drive the needle 22 into the eye. As the needle 22 is further inserted into the eye, a portion of the cannula 14 is inserted into the puncture. The needle 22 can then be withdrawn from the eye to leave the cannula 14 retained in the eye. The forces of the elastically deformed tissues surrounding the puncture can help to retain the cannula 14 in the eye.

The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention. For example, the interlocking features of the slide 18 and the ribs 30 are described with respect to a specific construction using projections engagable within recesses. Specifically, in some positions of the slide 18, a projection from the slide 18 or handle 16 is described as engaging a recess in the handle 16 or slide 18, respectively. In alternative embodiments, these interlocking engagements can be reversed.

As another example, the handle 16 described above and illustrated in the figures has a pair of arms 26 between which the slide 18 moves. Among other functions, the arms 26 serve to protect the needle 22 prior to use of the assembly 10. In other embodiments, the handle 16 can have other shapes in which the needle 22 is protected prior to use, some of which do not have a pair of arms 26 as described above. For example, the needle 22 and slide 18 can be received within a tubular element, whereby a portion of the slide 18 extends through an elongated aperture in the handle 16 and can be manipulated by a user to extend and retract the slide 18 as described above. As another example, the needle 22 and slide 18 can be received within a channel of a handle 16, whereby the slide 18 is accessible by a user to move the slide 18 to an extended position as described above. In such alternative embodiments, the handle 16 and slide 18 can still have any or all of the other features and elements described above with respect to the illustrated embodiment (e.g., projections 44, 58, 54, recesses 40, 42, 60, and the like).

As yet another example, the slide 18 illustrated in FIGS. 1-4 is slidable engaged with two arms 26. In other embodiments, the slide 18 can instead be slidably engaged with only one of the two arms 26, or can be slidably engaged with a handle having a single arm 26 and one or more other handle portions shielding the needle 22 when in the retracted position.

As described above, the ophthalmic trocar-cannula assembly 10 has a handle 16. It should be noted that the term "handle" does not indicate or imply that the ophthalmic trocar-cannula assembly 10 is restricted for use and manipulation by a human hand. The ophthalmic trocar-cannula assembly 10 can be mounted to any element or structure for manipulation in any other manner, such as by a robotic arm or other equipment.

Various features of the invention are set forth in the following claims.

I claim:

1. An ophthalmic trocar comprising:
a handle having a top surface and a bottom surface, the handle including
a body portion having a longitudinal axis extending along a longitudinal direction;
a pair of arms, each arm extending from the body portion in the longitudinal direction to a free, distal end such that the distal ends of each arm are not connected to one another and having an inner surface, the pair of arms at least partially defining a longitudinally extending aperture that is visible during use; and
a rib on each arm, each rib extending from the inner surface of its respective arm into the longitudinally extending aperture;
a slide positioned between the pair of arms, the slide having a channel configured to receive the rib, and movable along the ribs in the longitudinal direction between a retracted position and an extended position; and
a needle coupled to the slide and movable along with the slide between the retracted position and the extended position, the needle positioned substantially entirely within an outer periphery of the handle in the retracted position, at least a portion of the needle extending beyond the periphery of the handle in the extended position.

2. The ophthalmic trocar of claim 1, wherein the slide is interlocked with the rib in the retracted position of the slide to retain the slide in the retracted position.

3. The ophthalmic trocar of claim 2, wherein the slide has a projection releasably engagable with a recess in the rib to retain the slide in the retracted position.

4. The ophthalmic trocar of claim 3, wherein at least one of the projection and recess has a ramped surface to allow movement of the slide out of the retracted position by movement of the arms.

5. The ophthalmic trocar of claim 1, further comprising a projection extending from the handle into the elongated aperture, the projection positioned to block removal of a cannula positioned on the needle when the slide is in the retracted position.

6. The ophthalmic trocar of claim 1, wherein the slide is interlocked with the handle in the extended position of the slide to retain the slide in the extended position.

7. The ophthalmic trocar of claim 6, further comprising a projection extending from each arm into engagement with a respective recess on the slide when the slide is in the extended position.

8. The ophthalmic trocar of claim 7, wherein the slide is interlocked with the rib in the retracted position of the slide to retain the slide in the retracted position.

9. The ophthalmic trocar of claim 8, further comprising a projection extending from the slide into engagement with a recess on the handle when the slide is in the retracted position.

10. The ophthalmic trocar of claim 9, wherein the arms are elastically deformable to release the slide from the retracted position.

11. An ophthalmic trocar comprising:
a handle having a top surface and a bottom surface, the handle including
a body portion having a longitudinal axis extending along a longitudinal direction;
a pair of arms extending from the body portion in the longitudinal direction, the arms at least partially defining a longitudinally extending aperture that is visible during use, each arm having an inner surface, each of the arms having a first proximal end, integral with the body portion, and a free, distal end such that the distal ends of each arm are not connected to one another; and
a rib on each arm, each rib extending from the inner surface of its respective arm into the longitudinally extending aperture;
a slide positioned between the pair of arms, the slide having a channel configured to receive the rib, and movable along the ribs in the longitudinal direction between a retracted position and an extended position; and
a needle coupled to the slide and movable along with the slide between the retracted position and the extended position, the needle positioned substantially entirely within an outer periphery of the handle in the retracted position, at least a portion of the needle extending beyond the periphery of the handle in the extended position.

12. The ophthalmic trocar of claim 11, wherein the slide is interlocked with the rib in the retracted position of the slide to retain the slide in the retracted position.

13. The ophthalmic trocar of claim 12, wherein the slide has a projection releasably engagable with a recess in the rib to retain the slide in the retracted position.

14. The ophthalmic trocar of claim 13, wherein at least one of the projection and recess has a ramped surface to allow movement of the slide out of the retracted position by movement of the arms.

15. The ophthalmic trocar of claim 11, further comprising a projection extending from the handle into the elongated aperture, the projection positioned to block removal of a cannula positioned on the needle when the slide is in the retracted position.

16. The ophthalmic trocar of claim 11, wherein the slide is interlocked with the handle in the extended position of the slide to retain the slide in the extended position.

17. The ophthalmic trocar of claim 16, further comprising a projection extending from each arm into engagement with a respective recess on the slide when the slide is in the extended position.

18. The ophthalmic trocar of claim 17, wherein the slide is interlocked with the rib in the retracted position of the slide to retain the slide in the retracted position.

19. The ophthalmic trocar of claim 18, further comprising a projection extending from the slide into engagement with a recess on the handle when the slide is in the retracted position.

20. The ophthalmic trocar of claim 19, wherein the arms are elastically deformable to release the slide from the retracted position.

* * * * *

UNITED STATES PATENT AND TRADEMARK OFFICE
CERTIFICATE OF CORRECTION

PATENT NO. : 7,604,647 B2  
APPLICATION NO. : 10/971421  
DATED : October 20, 2009  
INVENTOR(S) : David E. Chen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 511 days.

Signed and Sealed this

Fifth Day of October, 2010

David J. Kappos  
*Director of the United States Patent and Trademark Office*